(12) United States Patent
De Block

(10) Patent No.: US 8,901,369 B2
(45) Date of Patent: Dec. 2, 2014

(54) INCREASE OF YIELD IN CROP PLANTS THROUGH SELECTION OF EPIGENETICALLY MODIFIED POPULATIONS

(75) Inventor: Marc De Block, Merelbeke (BE)

(73) Assignee: Bayer CropScience N.V., Diegem (BE)

( * ) Notice: Subject to any disclaimer, the term of this patent is extended or adjusted under 35 U.S.C. 154(b) by 213 days.

(21) Appl. No.: 13/378,536

(22) PCT Filed: Jun. 11, 2010

(86) PCT No.: PCT/EP2010/003507
§ 371 (c)(1),
(2), (4) Date: Dec. 15, 2011

(87) PCT Pub. No.: WO2011/000466
PCT Pub. Date: Jan. 6, 2011

(65) Prior Publication Data
US 2012/0117678 A1     May 10, 2012

Related U.S. Application Data

(60) Provisional application No. 61/221,186, filed on Jun. 29, 2009.

(30) Foreign Application Priority Data

Jul. 1, 2009   (EP) .................................... 09075284

(51) Int. Cl.
*A01H 1/00*   (2006.01)
*A01H 3/00*   (2006.01)

(52) U.S. Cl.
CPC ........................................ *A01H 3/00* (2013.01)
USPC .......................................... 800/260; 800/265

(58) Field of Classification Search
None
See application file for complete search history.

(56) References Cited

U.S. PATENT DOCUMENTS 4,003,156 A    1/1977    Sibi et al.

FOREIGN PATENT DOCUMENTS

WO        02066972       8/2002
WO       2010005298      1/2010

OTHER PUBLICATIONS

Nunes-Nesi et al, 2005, Plant Physiol., 137:611-622.*
De Block et al, 2002, Plant Physiol. Biochem., 40:845-852.*
Carrari et al, 2003, Plant Physiology, 133:1322-1335.*
Andrew Bottley, et al., Variation for homoeologous gene silencing in hexaploid wheat, The Plant Journal, vol. 56, No. 297-302, 2008.
Gio Braidotti, Biotechnology—Epigenetics comes of age for plant breeders, Ground Cover Issue 70, Sep.-Oct. 2007.
Marc Deblock, The selection mechanism of phosphinothricin is influenced by the metabolic status of the tissue, Planta, vol. 197, No. 619-626, 1995.
Marc Deblock, et al., A simple and robust in vitro assay to quantify the vigour of oilseed rape lines and hybrids, Plant Physiol, Biochem, vol. 40, No. 845-852, 2002.
F.D. Enfield, et al., Mutational variance for pupa weight in *Tribolium castaneum*, Theor Appl Genet, vol. 77, No. 416-420, 1989.
F.D. Enfield, et al., Selection for pupa weight in *Tribolium castaneum*, Genetics, vol. 54, No. 523-533, Aug. 1966.
Sophie Gutierres, et al., Lack of mitochondrial and nuclear-encoded subunits of complex I and alteration of the respiratory chain in *Nicotiana sylvestris* mitochondrial deletion mutants, Proc. Natl., Acad. Sci. USA, vol. 94, No. 3436-3441, Apr. 1997.
Miriam Hauben, et al., Energy use efficiency is characterized by an epigenetic component that can be directed through artificial selection to increase yield, PNAS, vol. 106, No. 47, Nov. 24, 2009.
Ian R. Henderson, et al., Epigenetic Inheritance in plants, Nature, vol. 447, May 24, 2007.
Eva Jablonka, et al., Transgenerational Epigentic inheritance: prevalence, mechanisms, and implications for the study of heredity and evolution, The Quarterly Review of Biology, vol. 84, No. 2, Jun. 2009.
Frank Johannes, Assessing the Impact of Transgenerational Epigenetic Variation on Complex Traits, Plos Genetics vol. 5 No. 6, Jun. 2009.
Izabela M. Juszczuk, et al., Effect of Mitochondrial genome rearrangement on respiratory activity, photosynthesis, photorespiration and energy status of MSC16 cucumber (*Cucumis sativus*) mutant, Physiologia Plantarum vol. 131, No. 527-541, 2007.
Pamela K. Kaufman, et al., Stabilizing Selection for Pupa Weight in *Tribolism castaneum*, Genetics, vol. 87, No. 327-341, Oct. 1977.
Edwin Kraus, et al., Yield advantage of a slow over a fast respiring population of *Lolium perenne* cv. S23 depends on plant density, New Phytol, vol. 123, No. 39-44, 1993.
Edwin Kraus, et al., The effect of handling on the yield of two populations of *Lolium perenne* selected for differences in mature leaf respiration rate, Physiologia Plantarum, vol. 89, No. 341-346, 1993.
Lewis N. Lukens et al., The plant genome's methylation status and response to stress: implications for plant improvement, Current Opinion in Plant Biology, vol. 10, No. 317-322, 2007.
A. Harvey Millar, et al., Control of Ascorbate Synthesis by Respiration and Its Implications for Stress Responses, Plant Physiology, Oct. 2003, vol. 133, No. 443-447.
Jean Molinier, et al., Transgeneration memory of stress in plants, Nature, vol. 442, Aug. 2006.
David A. Musser, et al., The use Tetrazolium Salts to Determine Sites of Damage to the Mitochondrial Electron Transport Chain in Intact Cells Following in vitro Photodynamic Therapy with Photofrin II, Photochemistry and Photobiology, vol. 59, No. 6, pp. 621-626, 1994.
Jun Nakamura, et al., Quantitation of Intracellular NAD(P)H can monitor an imbalance of DNA single strand break repair in base excision repair deficient cells in real time, Nucleic Acids Research, vol. 31, No. 17, 2003.
Adriano Nunes-Nesi, et al., Enhanced Photosynthetic Performance and Growth as a Consequence of Decreasing Mitochondrial Malate Dehydrogenase Activity in Transgenic Tomato Plants, Plant Physiology, Feb. 2005, vol. 137, No. 611-622.

(Continued)

*Primary Examiner* — David H Kruse
*Assistant Examiner* — Jason Deveau Rosen

(57) ABSTRACT

Methods are provided to select plants and populations of epigenetically fixed crop plants with improved yield.

17 Claims, 8 Drawing Sheets

(56) References Cited

OTHER PUBLICATIONS

Bernard Pineau, et al., Galactono-1, 4 lactone Dehydrogenase is Required for the Accumulation of Plant Respiratory Complex I, Journal of Biological Chemistry vol. 283, No. 47, Nov. 21, 2008.

P. Priault, et al., The lack of mitochondrial complex I in a CMSII mutant of *Nicotiana sylvestris* increases photorespiration through an increased internal resistance to CO2 diffusion, Journal of Experimental Botany, vol. 57, No. 12, 3195-3207, 2006.

Peter R. Rich, et al., The sites of interaction of triphenyltetrazolium chloride with mitochondrial respiratory chains, Federation of European Microbiological Societies, 2001, vol. 202, pp. 181-187.

Mohammed Sabar, et al., Complex I Impairment, Respiratory Compensations, and Photosynthetic Decrease in Nuclear and Mitochondrial Male Sterile Mutants of *Nicotiana sylvestris*, Plant Physiology, vol. 124, No. 1239-1249, Nov. 2000.

Nathan M. Springer, et al., Epigenetics: The second Genetic Code, Aadvances in Agronomy, vol. 100, 2008.

D. Wilson, Response to Selection for Dark Respiration Rate of Mature Leaves in *Lolium perenne* and its Effects on Growth of Young Plants and Simulated Swards, Ann. Bot., vol. 49, p. 303-312, 1982.

D. Wilson, et al., Effect of Selection for Dark Respiration Rate of Mature Leaves on Crop Yields of Rate of *Lolium perenne* cv. S23, Ann. Bot., vol. 49, p. 313-320, 1982.

Daniel Zilberman et al., Epigenetic inheritance in *Arabidopsis*: selective silence, Current Opinion in Genetics & Development, vol. 15, p. 557-562, 2005.

\* cited by examiner

INCREASE OF YIELD IN CROP PLANTS THROUGH SELECTION OF EPIGENETICALLY MODIFIED POPULATIONS

CROSS-REFERENCE TO RELATED APPLICATIONS

This application is a §371 U.S. National Stage of International Application No. PCT/EP2010/003507, filed Jun. 11, 2010, which claims the benefit of European Patent Application Serial No. 09075284.1, filed Jul. 1, 2009, U.S. Patent Application Ser. No. 61/221,186, filed Jun. 29, 2009, the contents of which are herein incorporated by reference in their entirety.

FIELD OF THE INVENTION

The invention relates to the field of agriculture. More specifically, methods are provided to select populations of plants, including crop plants, exhibiting a high energy use efficiency or high energy use efficiency combined with drought tolerance and which differ only in their epigenetic state, allowing to increase yield of such selected and epigenetically different populations compared to unselected populations. Also provided are epigenetically different plants and populations of plants exhibiting high energy use efficiency, which may be identified by their combined lower cellular respiration rate and higher energy content of the cells, by their increased content of ascorbate and/or increased content of Complex I in the mitochondrial respiratory chain. Further provided are epigenetically different plants and populations of plants exhibiting high energy use efficiency combined with drought tolerance. The epigenetic modifications can be fixed and transmitted to subsequent generations. It has also been found that the epigenetic energy use efficiency component can be added on top of hybrid vigor and can result in higher yielding hybrids.

BACKGROUND

The production of agricultural goods and in particular food and feed production, in sufficient quantity and quality is an increasingly challenging task. One the one hand, there is a continuous growth of the demand for agricultural products, due to increase in world population as well as increase in the average standard of living for large parts of the world population. On the other hand, the area suitable or available for agriculture is continuously shrinking, partly because of changing climate conditions which can result in deterioration of areas previously suitable for agriculture. A continuous demand exists to increase the yield potential of agricultural crops, or at least maintaining such yield potential when growing agricultural crops under suboptimal or adverse abiotic conditions.

Up to now, efforts to increase the intrinsic yield potential have mainly focused on exploiting the genetic variability within the crops. By traditional breeding techniques existing or induced variant alleles are shuffled into new combinations. More recently, the pool of variability has been expanded through molecular techniques allowing the exchange of genetic material across species, and even kingdom, barriers.

However, much less attention has been devoted to the role epigenetic control mechanisms may play in determining quantitative traits such as yield. Indeed, all quantitative traits such as size and weights in animals or yield, particularly seed yield in crops exhibit variability with a normal distribution, even within a population of genetically identical individuals. Underlying the observed phenotypic variability are genetic components, environmental factors but also epigenetic components. The importance in plants of epigenetic control components in short and long term adaptation to stress has been documented (Molinier et al. 2006, Transgeneration memory of stress in plants. *Nature* 442, 1046-1049). Furthermore, it has been demonstrated that altered epigenetic states can be transmitted to successive generations that have not been or are no longer exposed to the inducing trigger (also reviewed in Jablonka and Raz, 2009 Transgenerational epigenetic inheritance: prevalence, mechanisms, and implications for the study of heredity and evolution. *The Quarterly Review of Biology* 84, No. 2, 131-176).

There is no direct proof however that recurrent selection allows to drive the epigenetic component of a quantitative trait towards the ends of the normal distribution curve. In other words, the prior art remains silent on the ability to influence or select from a population, particularly from a genetically uniform population, those individuals with an above or below average value for the quantitative trait and fix that selected epigenetic component in a (sub)population.

Enfield and colleagues (Enfield, F. D., Comstock, R. E. & Braskerud, O, Selection for pupa weight in *Tribolium castaneum*. I. Parameters in base populations. *Genetics* 54, 523-533 (1966); Kaufman, P. K. & Enfield, F. D., Comstock, R. E. Stabilizing selection for pupa weight in *Tribolium castaneum*. *Genetics* 87, 324-341 (1977) described experiments whereby starting from a population obtained through a cross between two inbred flour beetles with an average pupa weight of 2400 µg, they were able to select a population with an average pupa weight of 5800 µg by continuous inbreeding for 120 generations. Enfield et al expressed their surprise that so many genetic variability was maintained over so many generations of inbreeding. It is however not unlikely that at a certain stage of the selection process epigenetic variability rather than genetic variability was selected for. This is further supported by identical experiments starting with inbred lines that were homozygous for the genes affecting pupa weight (Enfield, F. D. & Braskerud, O. Mutational variance for pupa weight in *Tribolium castaneum*. *Theor. Appl. Genet.* 77, 416-420 (1989)).

Various parameters have been employed to establish a correlation with the yield potential of a plant. A positive correlation has been found between yield potential and lower cellular respiration rates.

Wilson described the response to selection of dark respiration rate of mature leaves in *Lolium perenne* and its effects on growth of young plants and simulated swards. (Wilson *Ann. Bot.* 49, 303-312 (1982))

Wilson and Jones described the effect of selection for dark respiration rate of mature leaves on crop yields of *Lolium perenne* cv. S23. (Wilson and Jones *Ann. Bot.* 49, 313-320 (1982)).

Kraus et al. reported on the yield advantage of a 'slow-' over a 'fast-' respiring population of *Lolium perenne* cv. S23 which depends on plant density. (Kraus et al. *New Phytol.* 123, 39-44 (1993)) and on the effect of handling on the yield of two populations of *Lolium perenne* selected for differences in mature leaf respiration rate (Kraus et al. *Physiol. Plant.* 89, 341-346 (1993)).

Nunes-Nesi et al. described enhanced photosynthetic performance and growth as a consequence of decreasing mitochondrial malate dehydrogenase activity in transgenic tomato plants. (Nunes-Nesi et al. Plant Physiol. 137, 611-622 (2005)). Juczczuk et al. reported on the effect of mitochondrial genome rearrangement on respiratory activity, photosynthesis, photorespiration and energy status of MSC16 cucumber (*Cucumis sativus*) mutant. (Juczczuk et al, Physiol. Plant. 131, 527-541 (2007)).

De Block and De Brouwer described a simple and robust in vitro assay to quantify the vigour of oilseed rape lines and hybrids. (Plant Physiol. Biochem. 40, 845-852 (2002))

WO02/066972 provides methods and means for determining parent inbred plant lines with good combining ability, for determining good combinations of parent inbred plant lines capable of yielding hybrid lines with high heterosis, and further for determining the agronomical performance of different plant lines, which can be performed in vitro by determining the electron flow in the mitochondria under control and stress conditions None of the prior art documents however described recurrent selection for low cellular respiration rates in a genetically uniform population of plants which allows to establish (sub)populations of plants which have a higher yield potential and tolerance to adverse biotic conditions. The epigenetic component can further be inherited in successive generations (and behaves as a dominant or co-dominant factor).

SUMMARY OF THE INVENTION

In one embodiment of the invention a method of selecting a population of plants, such as *Brassica* oilseed rape, tomato plants or rice plants, or seeds thereof with a high energy use efficiency comprising the following steps:
  a. providing an population consisting of a plurality of individual plants which are genetically uniform;
  b. isolating a tissue sample or explant from individual plants of said population in a manner which allows further cultivation of said sampled individual plants;
  c. optionally, culturing said tissue samples or explants under conditions which activate the metabolism in said plants;
  d. determining the cellular respiration rate of said individual plants by analyzing said samples of said plants;
  e. selecting a number of plants wherein said sample exhibits a cellular expiration which is lower, preferably is significantly lower, than the average cellular respiration of samples from said population;
  f. growing the selected plants and propagating from each of the selected plants a line of cloned progeny plants;
  g. determining the energy use efficiency for each line of cloned progeny plants;
  h. selecting a line of clone plants wherein said energy use efficiency is higher, than the average of the energy use efficiency of all lines of cloned progeny plants, preferably select the line of clone progeny plants with the highest energy use efficiency;
  i. growing a population of individual plants from said selected line of clone progeny plants; and
  j. reiterating at least once steps b to i on said subsequent population.

The energy use efficiency can be determined by determining the cellular respiration and determining the NAD(P)H content in the isolated sample and dividing the NAD(P)H content by the respiration to determine the energy use efficiency. The energy use efficiency can also be determined by measuring the ascorbate or ascorbic acid content of the plant or by measuring the respiratory chain complex I activity in said sample.

The provided methods include identifying plants with high energy use efficiency by determining the cellular respiration in said sample and at least one of the following parameters: ascorbate content; NAD(P)H content; respiratory chain complex I activity; or photorespiration; and selecting those plants with lower cellular respiration and a higher ascorbate content, or a higher respiratory chain complex I activity or lower photorespiration than the control plants (i.e. plants of the original population which have not been subjected to the repeated selection scheme for low cellular respiration). Typically cellular respiration rate may be between 85 and 95% of the cellular respiration rate of a control plant and NAD(P)H content may be between 95 to 105% of the NAD(P)H content of a control plant. Respiratory chain complex I activity may typically be between 120 to 140% of the respiratory chain complex I activity of a control plant and ascorbate content may be between 150 to 220% of the ascorbate content of a control plant. Photorespiration is preferably between 80 to 92% of the photorespiration of a control plant.

The invention also provides a method for producing a population of plants or seeds with increased yield potential which comprises selecting from a population of individual plants which are genetically uniform, those plants or a subpopulation of plants or seeds with a high energy use efficiency according to the selection methods herein presented. The selected plants may be further crossed with other plants to obtain progeny with high energy use efficiency and increased yield potential.

In another embodiment of the invention a method is provided for producing a population of plants or seeds with increased vigor and/or increased tolerance to adverse abiotic conditions which comprises selecting from a population of individual plants which are genetically uniform, those plants or a subpopulation of plants or seeds with a high energy use efficiency according to the selection methods herein presented. The selected plants may be further crossed with other plants to obtain progeny with high energy use efficiency and with increased vigor and/or increased tolerance to adverse abiotic conditions.

In another embodiment of the invention, a method is provided for increasing harvest yield, including the steps of producing a subpopulation of plants or seeds with high energy use efficiency from a genetically uniform population by repeated selection for low cellular respiration; growing the plants or seeds in a field; and producing a harvest from those plants or seeds.

In yet another embodiment of the invention, a method for producing a hybrid plant or hybrid seed with high yield or tolerance to adverse abiotic conditions is provided, which comprises the following steps:
  a. selecting a population of plants with high energy use efficiency according to the selection methods herein mentioned for at least one parent inbred plant, including for at least both parent inbred plants; and if one parent plant is a male sterile plant and maintaining said male sterile plant requires the use of a maintainer line, optionally also for the maintainer line;
  b. crossing plants of said population with another inbred plant;
  c. isolating hybrid seed of said cross; and
  d. optionally, grow hybrid plants from said seed.

In yet another embodiment of the invention a plant, seed or population of plants selected by one of the herein described methods is provided.

Thus, the invention provides plants, including hybrid plants, such as *Brassica* oilseed rape, tomato plants or rice plants, or seeds thereof, with high energy use efficiency characterized in that the plant has a low cellular respiration, such as a cellular respiration rate is between 85 and 95% of the cellular respiration rate of a control plant, and at least one, more, or all of the following characteristics:

i. a high ascorbate content which may be between 150 to 220% of the ascorbate content of a control plant;
ii. a high NAD(P)H content, which may be between 95 to 105% of the NAD(P)H content of a control plant;
iii. a high respiratory chain complex I activity, which may be between 120 to 140% of the respiratory chain complex I activity of a control plant; or
iv. a low photorespiration which may be between 80 to 92% of the photorespiration of a control plant;

whereby control plants are plants of the genetically uniform population which have not been subjected to the repeated selection scheme for low cellular respiration rate.

DETAILED DESCRIPTION OF VARIOUS EMBODIMENT OF THE INVENTION

Figure 1:
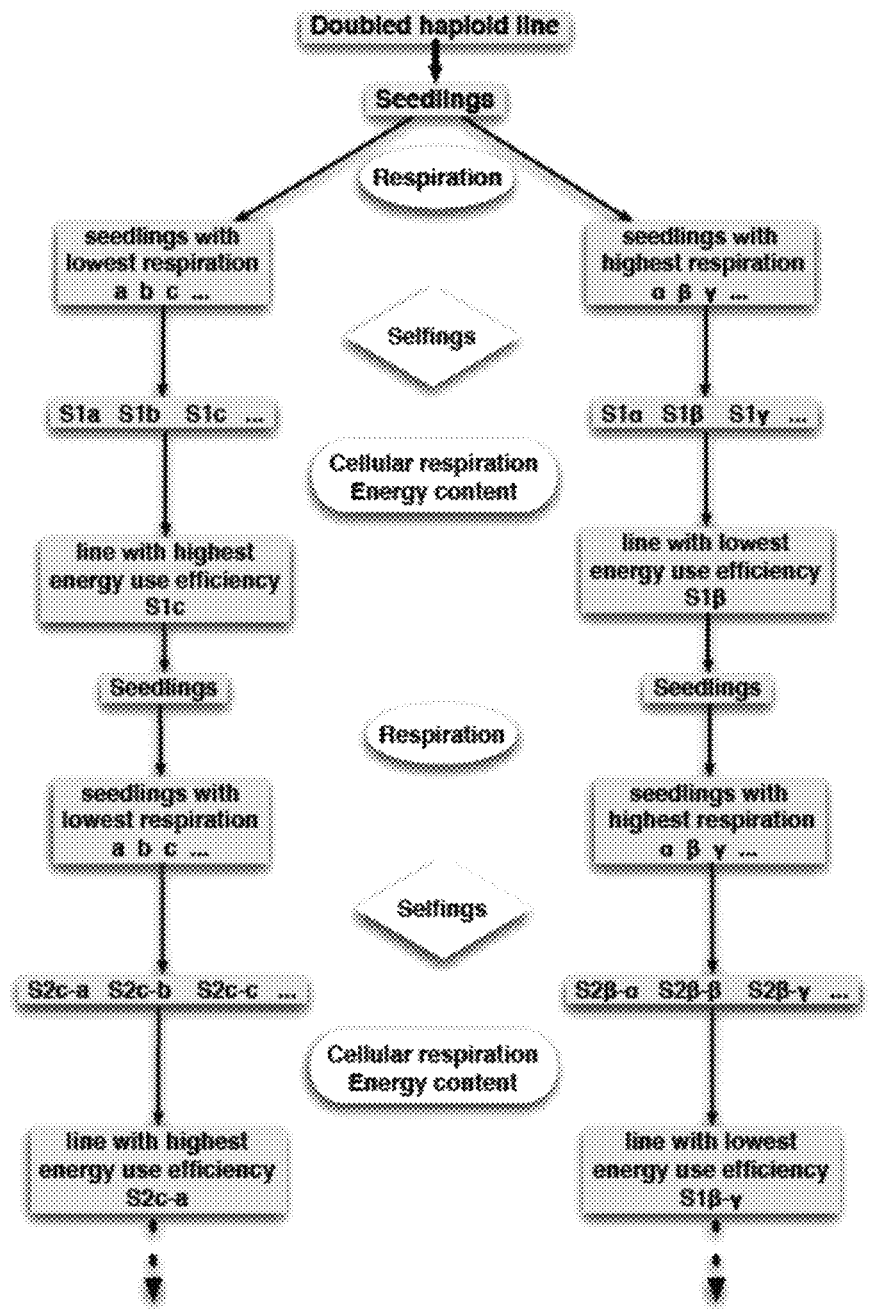
FIG. 1: Selection scheme for the isolation of subpopulations of canola which differ in cellular respiration and energy use efficiency in canola.
The selection was started from an isogenic doubled haploid line. About five selected individual plants with the lowest respectively highest respiration were selfed and the progeny was individually tested for respiration and energy use efficiency. The selection was continued with the populations having the highest respectively lowest energy use efficiency.

The current invention is based on the following unexpected observations by the inventor:

a. A correlation exists between low respiration, particularly low respiration and high energy content i.e. high energy use efficiency and yield potential, even between individual plants in a genetically uniform population.

b. The epigenetic compounds controlling high energy use efficiency in a genetically uniform population can be fixed by recurrent selection for individual plants with high energy use efficiency and propagation of progeny of such plants leading to subpopulations of plants wherein the energy use efficiency is higher than in the original starting population and wherein the high energy use efficiency phenotype is stably transmitted to successive generations.

c. The epigenetically determined high energy use efficiency phenotype can be transmitted upon crossing with unselected population and behaves as dominant or co-dominant character.

d. The epigenetically controlled high energy use efficiency phenotype can be selected for in parent inbred lines (and/or maintainer lines) and provides for an additional yield potential increase in the hybrid offspring (in excess of hybrid vigor).

e. The high energy use efficiency phenotype is correlated with a high complex I activity and ascorbic acid content, which can thus be regarded as indicators of high energy use efficiency.

f. The high energy use efficiency phenotype is inversely correlated with photorespiration.

In a first embodiment of the invention, a method is provided which allows the selection of a (sub)population of plants with a high energy use efficiency ("EUE") and thus a high yield, particularly seed yield potential from an initial population of genetically uniform individual plants. High energy use efficiency is a quantitative trait for which variability (along a normal distribution curve) exists within a population of genetically uniform plants. The method comprises the following steps:

a. providing an population consisting of a plurality of individual plants which are genetically uniform;
b. isolating a tissue sample or explant from individual plants of said population in a manner which allows further cultivation of said sampled individual plants;
c. optionally, culturing said tissue samples or explants under conditions which activate the metabolism in said plants;
d. determining the cellular respiration rate of said individual plants by analyzing said samples of said plants;
e. selecting a number of plants wherein said sample exhibits a cellular expiration which is lower, preferably is significantly lower, than the average cellular respiration of samples from said population;
f. growing the selected plants and propagating from each of the selected plants a line of cloned progeny plants;
g. determining the energy use efficiency for each line of cloned progeny plants;
h. selecting a line of clone plants wherein said energy use efficiency is higher, than the average of the energy use efficiency of all lines of cloned progeny plants, preferably select the line of clone progeny plants with the highest energy use efficiency;
i. growing a population of individual plants from said selected line of clone progeny plants; and
j. reiterating at least once steps b to i on said subsequent population.

As used herein "a population of genetically uniform plants" is a population of plants, wherein the individual plants are true breeding, i.e. show little or no variation at the genome nucleotide sequence level, at least for the genetic factors which are underlying the quantitative trait, particularly genetic factors underlying high energy use efficiency and low cellular respiration rate. Genetically uniform plants may be inbred plants but may also be a population of genetically identical plants such as doubled haploid plants. Doubled haploid plants are plants obtained by spontaneous or induced doubling of the haploid genome in haploid plant cell lines (which may be produced from gametes or precursor cells thereof such as microspores). Through the chromosome doubling, complete homozygous plants can be produced in one generation and all progeny plants of a selfed doubled haploid plant are substantially genetically identical (safe the rare mutations, deletions or genome rearrangements). Other genetically uniform plants are obtained by vegetal reproduction or multiplication such as e.g. in potato, sugarcane, trees including poplars or eucalyptus trees.

As used herein, "energy use efficiency" is the quotient of the "energy content" and "cellular respiration". High energy use efficiency can be achieved in plants when the energy content of the cells of the plant remains about equal to that of control plants, but when such energy content is achieved by a lower cellular respiration.

"Cellular respiration" refers to the use of oxygen as an electron acceptor and can conveniently be quantified by measuring the electron transport through the mitochondrial respiratory chain e.g. by measuring the capacity of the tissue sample to reduce 2,3,5 triphenyltetrazolium chloride (TTC). Although it is believed that for the purpose of the assays defined here, TTC is the most suited substrate, other indicator molecules, such as MTT (3-(4,5-dimethylthiazol-2-yl)-2,5 diphenyl-2H-tetrazolium), can be used to measure the electron flow in the mitochondrial electron transport chain (see Musser and Oseroff, 1994 *Photochemistry and Photobiology* 59, pp 621-626). TTC reduction occurs at the end of the mitochondrial respiratory chain at complex IV. Therefore, TTC reduction reflects the total electron flow through the mitochondrial respiratory chain, including the alternative oxidative respiratory pathway. The electrons enter the mitochondrial electron transport chain through complex I, complex II, and the internal and external alternative NAD(P)H dehydrogenases. A suitable TTC reduction assay has been described by De Block and De Brouwer, 2002 (*Plant Physiol. Biochem.* 40, 845-852).

The "energy content" of cells of a plant refers to the amount of molecules usually employed to store energy such as ATP, NADH and NADPH. The energy content of a sample can conveniently be determined by measuring the NAD(P)H content of the sample. A suitable assay has been described by Nakamura et al. 2003. (Quantification of intracellular NAD (P)H can monitor an imbalance of DNA single strand break repair in base excision repair deficient cells in real time. *Nucl. Acids Res.* 31, 17 e104).

Plants or subpopulations of plants should be selected wherein the energy use efficiency is at least as good as the energy use efficiency determined for the control plants, preferably is higher than the energy use efficiency of control plants. Although it is believed that there is no particular upper limit for energy use efficiency, it has been observed that subpopulations or plants can be obtained with a energy use efficiency which is about 5% to about 15%, particularly about 10% higher than the energy use efficiency of control plants. As used herein, control plants or control population are a population of plants which are genetically uniform but which have not been subjected to the reiterative selection for plants with a higher energy use efficiency.

Plants or subpopulations of plants can initially be selected for a cellular respiration which is lower than the cellular respiration determined for the control plants. Typically, plants with a high energy use efficiency have cellular respiration rate which is between 85 and 95% of the cellular respiration rate of control plants. It has been observed that it is usually feasible to subject a population with lower respiration rates to an additional cycle of selection yielding a population of plants with even lower respiration rates, wherein however the energy content level is also declined. Such selected population of plants have a yield potential which is not better than a population of unselected control plants and the yield may even be worse in particular circumstances. Selection of populations with too low cellular respiration, particularly when accompanied with a decline in energy content level is not beneficial. Respiration rates below 75% of the respiration rate of control plants, particularly combined with energy contents below 75% of the energy content of control plants should preferably be avoided.

The methods to select subpopulation of plants or plants with high energy use efficiency described herein are typically reiterated at least once; however, plants may be subjected to at least three or four or five cycles of selection. To avoid selecting plants or population of plants with a too low respiration cycle, it is expected that more than five cycles of selection should be avoided (depending on the plant species).

It has been observed that selected populations with a high energy use efficiency are also characterized by an increased respiratory chain complex I activity compared to control plants and by an increased ascorbic acid content compared to control plants. These characteristics could serve as an alternative or supplementary marker to select plants or (sub)populations of plants with increased energy use efficiency. Ascorbate content can be quantified using the reflectometric ascorbic acid test from Merck (Darmstadt, Germany). Complex I activity can be quantified using the MitoProfile Dipstick Assay kit for complex I activity of MitoSciences (Eugene, Oreg., USA).

It has been observed that the selected subpopulation were more tolerant to adverse abiotic conditions than the unselected control plants. Accordingly, the invention also provides a method for producing a population of plants or seeds with increased tolerance to adverse abiotic conditions by selection plants or populations of plants according to the methods described herein. As used herein "adverse abiotic conditions" include drought, water deficiency, hypoxic or anoxic conditions, flooding, high or low suboptimal temperatures, high salinity, low nutrient level, high ozone concentrations, high or low light concentrations and the like.

Furthermore, the selection methods according to the invention may be improved by simultaneously selecting for high energy use efficiency under condition mimicking adverse growth conditions. Drought tolerant plants with high energy use efficiency may be selected e.g. by including polyethyleenglycol, such as PEG6000, preferably in a range of 4 to 8%, specifically 5 to 7.5%, into the media used in the selection schemes herein described. Plants which are solely selected by growth on PEG containing media (without the determination and selection of the energy use efficiency) usually have a compact growth phenotype and develop thick cuticula and cell walls. The plants selected by combining growth on PEG6000 with high energy use efficiency have a normal growth phenotype but outperform control plants under drought conditions (see e.g. FIG. 13).

As the yield improvement obtained by selecting subpopulation of plants or plants with high energy use efficiency can be transmitted to subsequent generations in sexual crosses (behaving as a dominant or co-dominant factor) and as that yield improvement in hybrid plants moreover is additional to the normal yield increase due to hybrid vigor, a further embodiment of the invention provides a method for producing a hybrid plant or hybrid seed with high yield or tolerance to adverse abiotic conditions comprising:
  a. selecting a population of plants with high energy use efficiency according to the methods herein described for at least one parent inbred plant;
  b. crossing plants of that population with another inbred plant;
  c. isolating hybrid seed of the cross; and
  d. optionally, grow hybrid plants from the seed.

The selection scheme may further be applied to both parent lines and if hybrid production involves male sterility necessitating the use of a maintainer line for maintaining the female parent, the selection schemes described herein may also be beneficially used on the maintainer lines.

Preferably, the tissue samples or explants are hypocotyl explants, but other explants such as callus, shoots, leaf disks or whole leaves may be used to the same effect. For monocotyledonous plants, the leaf base of the first true leave is a suitable tissue sample or explant. It is further preferred that the explants should be derived from sterile in vitro grown material that has a high respiration rate or an active metabolism. This may be achieved by culturing or incubating the explants first on a medium comprising a suitable carbohydrate, such as sucrose, to enhance the respiration rate or metabolism. More preferably, explants are cultured on a callus inducing medium for a time sufficient to activate the metabolism, particularly for about 0 to 10 days, preferably for about 4 to 6 days, particularly for about 5 days. Preferably, the callus-inducing medium comprises sucrose, particularly about 2% to 3% w/w. Preferred temperature ranges for culturing the explants are about 24 to 25° C.

When the methods herein described are applied to sexually reproducing plants, the propagation step from each of the selected plants to yield a line of cloned progeny plants may be achieved by selfpollination (selfing) and harvest of the produced seeds. When the methods herein described are applied to vegetatively reproduced plants, the propagation step from each of the selected plants to yield a line of cloned progeny plants may be achieved by dividing the plants into suitable reproduction units and cultivation thereof until a complete plant is obtained.

The invention also provides selected plants or populations of plants with high energy use efficiency as can be obtained through the selection methods herein described. Such plants are characterized by a low cellular respiration (lower than the cellular respiration of control plants as herein defined) and at least one of the following characteristics: ascorbic acid higher than control plants; NAD(P)H content higher than control plants; respiratory chain complex I activity higher than control plants; and photorespiration lower than control plants.

The selection scheme has been successfully applied on rice plant populations, *Brassica napus* plant populations and *Lycopersicon esculentum* plant populations. Nevertheless, the methods and means described herein are believed to be suitable for all plant cells and plants, gymnosperms and angiosperms, both dicotyledonous and monocotyledonous plant cells and plants including but not limited to *Arabidopsis*, alfalfa, barley, bean, corn or maize, cotton, flax, oat, pea, rape, rice, rye, safflower, sorghum, soybean, sunflower, tobacco and other *Nicotiana* species, including *Nicotiana benthamiana*, wheat, asparagus, beet, broccoli, cabbage, carrot, cauliflower, celery, cucmber, eggplant, lettuce, onion, oilseed rape, pepper, potato, pumpkin, radish, spinach, squash, tomato, zucchini, almond, apple, apricot, banana, blackberry, blueberry, cacao, cherry, coconut, cranberry, date, grape, grapefruit, guava, kiwi, lemon, lime, mango, melon, nectarine, orange, papaya, passion fruit, peach, peanut, pear, pineapple, pistachio, plum, raspberry, strawberry, tangerine, walnut and watermelon *Brassica* vegetables, sugarcane, vegetables (including chicory, lettuce, tomato), Lemnaceae (including species from the genera Lemna, Wolffiella, Spirodela, Landoltia, Wolffia) and sugarbeet.

The following non-limiting Examples describe methods and means according to the invention. Unless stated otherwise in the Examples, all techniques are carried out according to protocols standard in the art.

EXAMPLES

Example 1

Methodology

Figure 9:
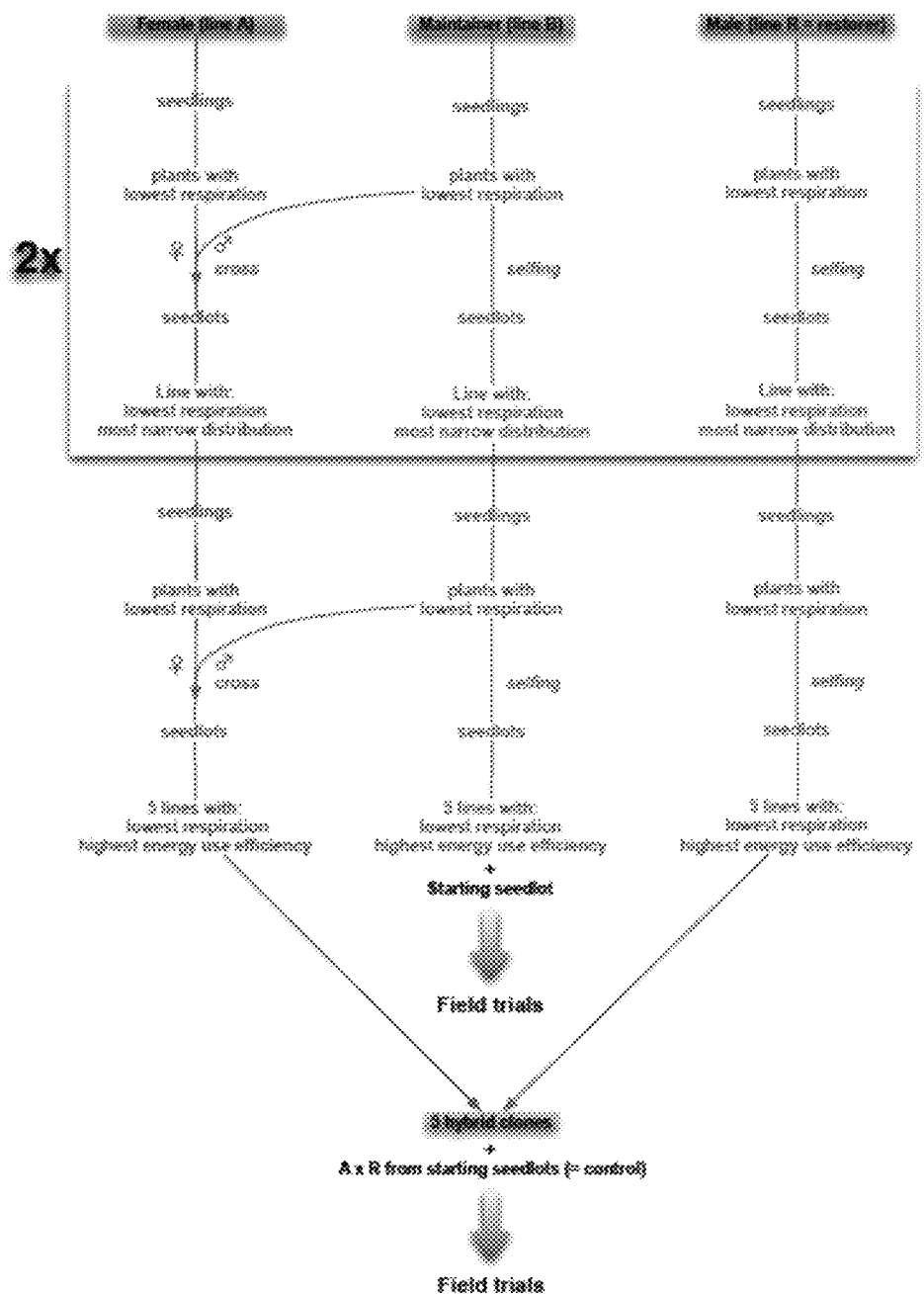
FIG. 9: Selection scheme for recurrent selection of high energy use efficient male, female and maintainer parent lines and generation of hybrids.

Artificial selection for respiration and EUE. Seedlings were grown in vitro for two weeks on agar medium half concentrated Murashige and Skoog medium supplemented with 2% sucrose. The shoot tips of the seedlings were put on the above medium for rooting, while five hypocotyl explants per seedling were cultured for five days on callus inducing medium (Murashige and Skoog medium supplemented with 3% sucrose and 1 mg/L 2,4-D, 0.25 mg/L NAA and 1 mg/L BAP). Cellular respiration of the hypocotyl explants was measured. The rooted shoot tips of about five seedlings with the highest respectively lowest respiration were transferred to the greenhouse for seed production by selfing. Both respiration and NAD(P)H content of about 35-40 seedlings of the obtained progenies were measured. Lines with the lowest, respectively, highest respiration and highest, respectively, lowest energy use efficiency were retained. The next rounds of selections were done in one direction for lower or higher respiration with lines having the lowest, respectively, highest respiration (FIG. 1). Three to five rounds of selection are sufficient to generate lines with distinct respiration and EUE. The selection for respiration and EUE in the hybrid seed production is represented in FIG. 9.

Physiological and biochemical assays. Cellular respiration of hypocotyl explants was quantified by measuring the reduction of 2,3,5-triphenyltetrazoliumchloride (TTC) as described (De Block and De Brouwer, supra). Total NAD(P)H content was quantified as described (Nakamura et al. supra). Energy use efficiency is expressed as the ratio of the % normalized values versus the control of NAD(P)H content to amount of reduced TTC. Ascorbate content was quantified using the reflectometric ascorbic acid test from Merck (Darmstadt, Germany). Complex I activity was quantified using the MitoProfile Dipstick Assay kit for complex I activity of MitoSciences (Eugene, Oreg., USA). The intensity of the photorespiration was measured in vitro by floating cotyledons or leaf pieces on ammonium free medium containing 3-5 mg/L glufosinate. Incubation was done for 24 hours in continuous light (about 70 μmol m$^{-2}$ sec$^{-1}$). The ammonium production was quantified as described (De Block et al., 1995. The selection mechanism of phosphinothricin is influenced by the metabolic status of the tissue. *Planta* 197, 619-626). Photorespiration was expressed as percent produced ammonium versus control.

Field trials. Field trials were performed on five locations with different soil qualities (from sandy to loamy soil). Each location contained six plots per line. Each plot was 10 m$^2$ in size, with different arrangement of the plots for each location. Yield was expressed as kg seed/plot.

Statistics. Data were statistically analysed by one-way ANOVA with Dunnett's post test using Prism version 5.00 (GraphPad Software, San Diego, USA).

Example 2

Figure 2:
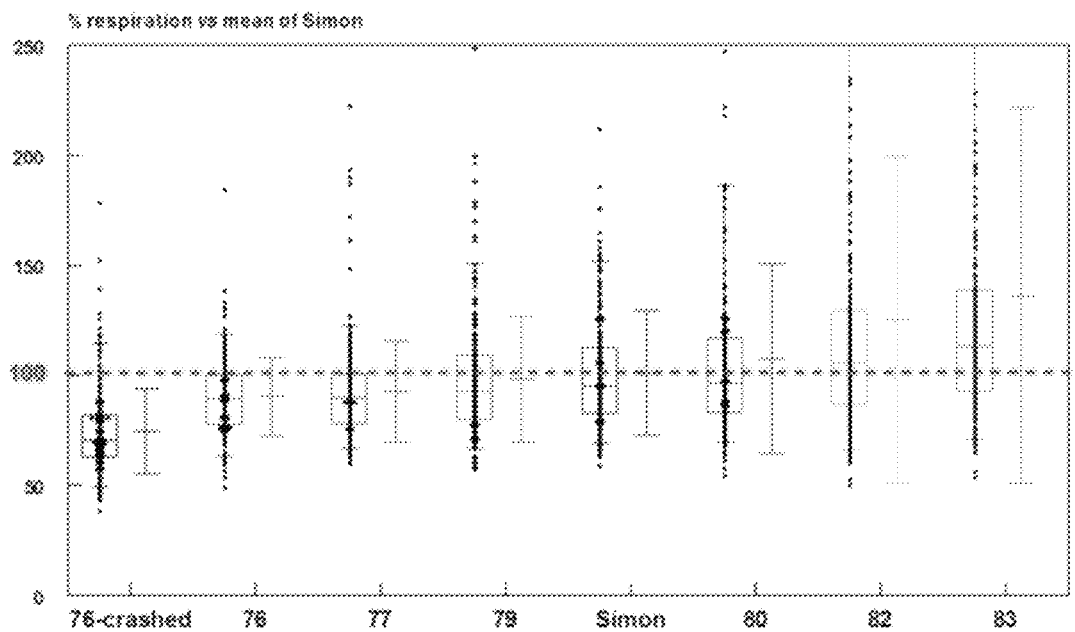
FIG. 2: Respiration of six selected canola populations versus the original starting population. The values were % normalized versus the average of the starting line 'Simon'. Each dot represents data obtained from an individual plant. Each population contains about 200 plants. The bar in the boxes represents the median of the population. The bars represent the standard deviation with indication of the mean.

Selection and Characterization of Selected *Brassica napus* Plants with High and Low Energy Use Efficiency Starting from an isogenic doubled haploid *B. napus* line to eliminate variation due to differences at the genetic level, seedlings with the lowest and highest cellular respiration were identified and retained (see 'Methods Summary'-FIG. 1 shows a schematic presentation of the selection scheme). In summary, starting from 200 seedlings from the doubled haploid population 'Simon' seedlings with the lowest and highest cellular respiration were identified and retained. Rooted shoot tips of five seedlings with the highest and lowest respiration, respectively, were transferred to the greenhouse for seed production by selfing. Two populations with respectively the lowest and highest EUE were identified. These two populations were the starting material for five additional rounds of selection for lines with higher and lower respiration rates, respectively. FIG. 2 shows the respiration of six lines that were generated: four lines with lower (LR76, LR76-crashed, LR77, LR79) and three lines with a higher respiration (HR80, HR82, HR83) versus the control from which the selection has been started. The 'LR76-crashed' line is derived from a further selection for lower respiration starting from line LR76. As will be shown below, the respiration of line LR76-crashed dropped below a critical threshold, resulting in a reduced vigor. At the individual plant level, there is a high variation in the high respiring lines (e.g line HR82 with a mean of 125% versus control and a standard deviation of 74%), while this variation is minimal in the low respiring lines (e.g. line LR76 with a mean of 90% versus the control and a standard deviation of 18%). From a breeder's point of view, the high variation in the high respiring lines indicates a negative behavior, while the limited variation in the low respiring lines would be scored as positive. The high efficiency with which these lines were generated (started from only 200 seedlings per selection cycle), suggests that no mutations are involved. Extensive AFLP-analyses could not identify differences between these lines and the control, except for the very high respiring line HR83 in which some chromosome deletions and inversions were detected. These plants regularly showed abnormal development and sterility. Therefore, HR83 was not retained for further analyses, together with LR79, because of its similar respiratory rate compared to the control.

Figure 3:
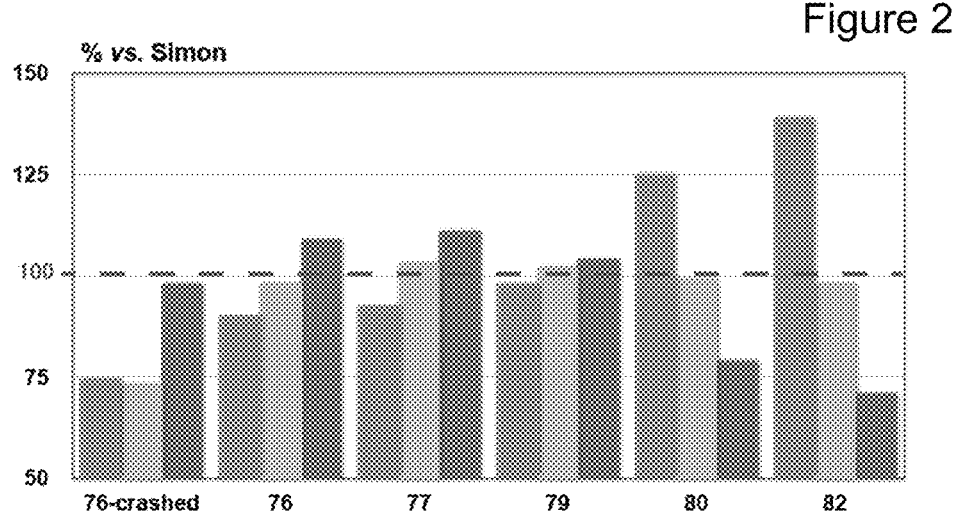
FIG. 3: Energy use efficiency of six selected canola populations. The values were % normalized versus the average of the starting line 'Simon'. The medium gray bars (left) represent the values obtained for respiration; the light gray bars (middle) represents the value obtained for energy content (NAD(P)H content); the dark gray bars (right) represent the energy use efficiency (NAD(P)H content divided by respiration).

It was expected that high cellular respiration would be linked to high energy production and vice versa. However, when the total amount of NAD(P)H, reflecting the energy content, was measured (Table 1; FIG. 3), it was noticed that lines with higher respiration had lower NAD(P)H levels. Lines with a lower respiration had a higher NAD(P)H content, except for line 'LR76-crashed'. When the ratio NAD(P)H versus respiration (energy use efficiency (EUE)) is calculated an inverse correlation is found between respiration and EUE except for the line LR76-crashed (Table 1—FIG. 3). Probably, the respiration in line LR76-crashed dropped below a critical threshold to maintain sufficient energy production.

Figure 6:
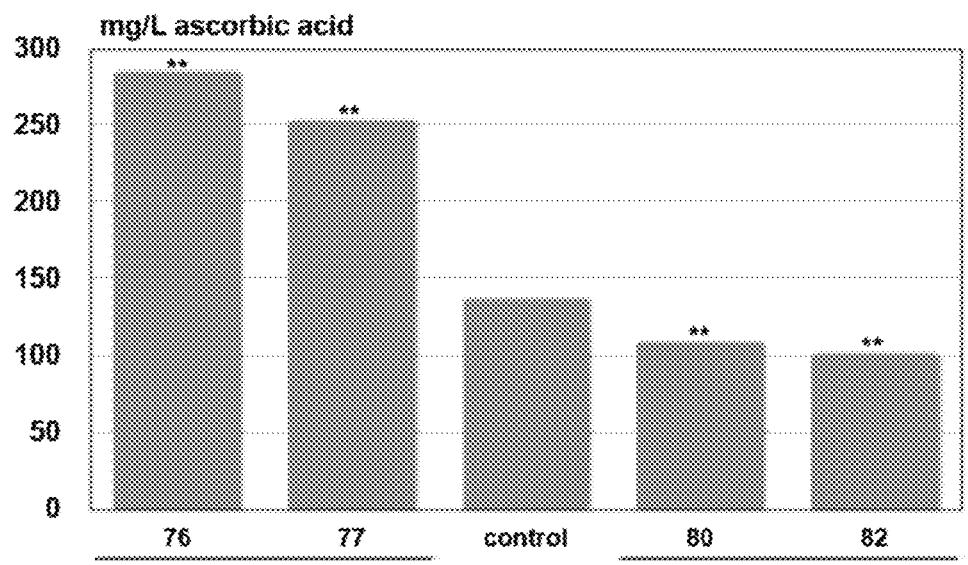
FIG. 6: Correlation between energy use efficiency and ascorbic acid content in selected canola populations. Ascorbic acid content is expressed in mg/L; ** $p<0.01$.

During the selection procedure, respiration was quantified by measuring the reduction of 2,3,5-triphenyltetrazolium chloride (TTC) by hypocotyl explants. TTC reduction occurs at the end of the mitochondrial respiratory chain at complex IV (Rich, P. R., Mischis, L. A., Purton, S. & Wiskich, J. T. The sites of interaction of triphenyltetrazolium chloride with mitochondrial respiratory chains. *FEMS Microbiol. Lett.* 202, 181-187 (2001)). Therefore, TTC reduction reflects the total electron flow through the mitochondrial respiratory chain, including the alternative oxidative respiratory pathway. The electrons enter the mitochondrial electron transport chain through complex I, complex II, and the internal and external alternative NAD(P)H dehydrogenases. The activity of complex I, being the main dehydrogenase, was measured in the 3rd leaf of control and selected lines (Table 1). An inverse correlation between respiration and complex I activity was found. Recently, it was found that L-galactono-1,4-lactone dehydrogenase, the last enzyme of the plant ascorbate biosynthesis pathway, is associated with an 800-kDa subcomplex of complex I and has an important function in the accumulation of complex I as *Arabidopsis* null-mutants for L-galactone-1,4-lactone dehydrogenase fail to accumulate complex I (Pineau et al. L-galactono-1,4-lactone dehydrogenase is required for the accumulation of plant respiratory complex I. *J. Biol. Chem.* 283, 32500-32505 (2008); Millar et al. Control of ascorbate synthesis by respiration and its implications for stress responses. *Plant Physiol.* 133, 443-447 (2003)). This apparent interrelation between ascorbate biosynthesis and complex I accumulation prompted us to measure the ascorbate content in the leaves of the different lines (Table 1—FIG. 6). The lines with the highest respiration and the lowest complex I activity have the lowest ascorbate content. The reverse is also true, the lines with a low respiration and a high complex I activity have a high ascorbate content. In summary, these results suggest that lines with a high, respectively low respiratory rate have a reduced, respectively increased complex I content. The high respiring lines resemble the cytoplasmic male sterile II (CMSII) mutant of Nicotiana sylvestris that lacks NAD7 subunit of complex I (Guitierres et al. Lack of mitochondrial and nuclear-encoded subunits of complex I and alteration of the respiratory chain in Nicotiana sylvestris mitochondrial deletion mutants. Proc. Natl. Acad. Sci. USA 94, 3436-3441 (1997); Sabar et al. Complex I impairment, respiratory compensations, and photosynthetic decrease in nuclear and mitochondrial male sterile mutants of Nicotiana sylvestris. Plant Physiol. 124, 1239-1249 (2000))[5]. The CSMII mutant has no complex I activity but still have a high respiration due to the compensatory enhanced activity of complex IV (cytochrome oxidase). The high respiration is probably due to an enhanced activity of the alternative NAD(P)H dehydrogenases to meet the ATP needs of the cell. Lines with a high complex I content are more efficient in producing ATP resulting in a lower respiratory rate.

Figure 4:
FIG. 4: Tolerance of selected canola populations to high temperature. Plants were subjected for 10 days to 45° Celsius prior to the taking of the photograph. Plants on the left are from a population selected to have low energy use efficiency; plants on the right are from a population selected to have high energy use efficiency.
Figure 5:
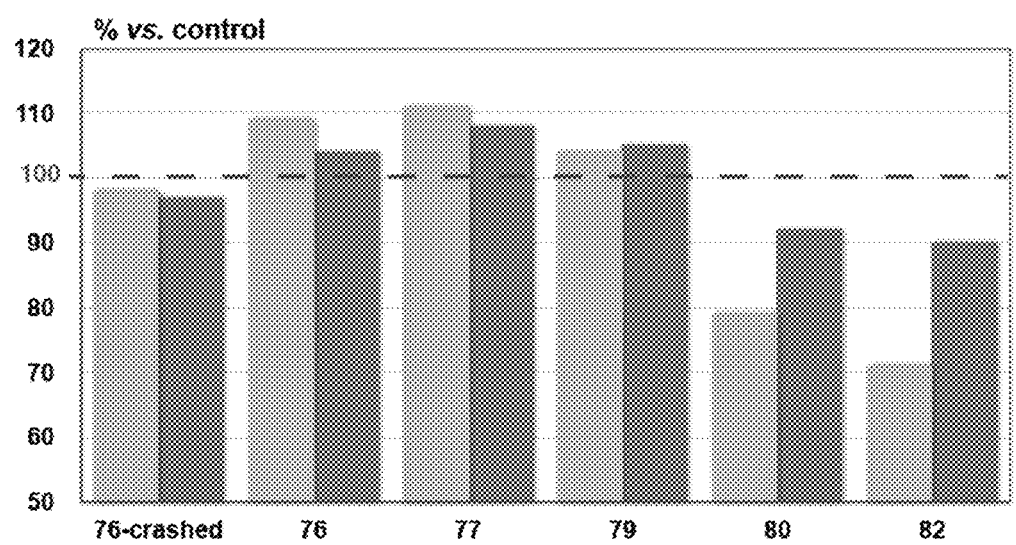
FIG. 5: Correlation between energy use efficiency and seed yield in selected canola populations. The values were % normalized versus the average of the starting line 'Simon'. Light gray bars represent the normalized energy use efficiency while the dark gray bars represent the seed yield.
Figure 7:
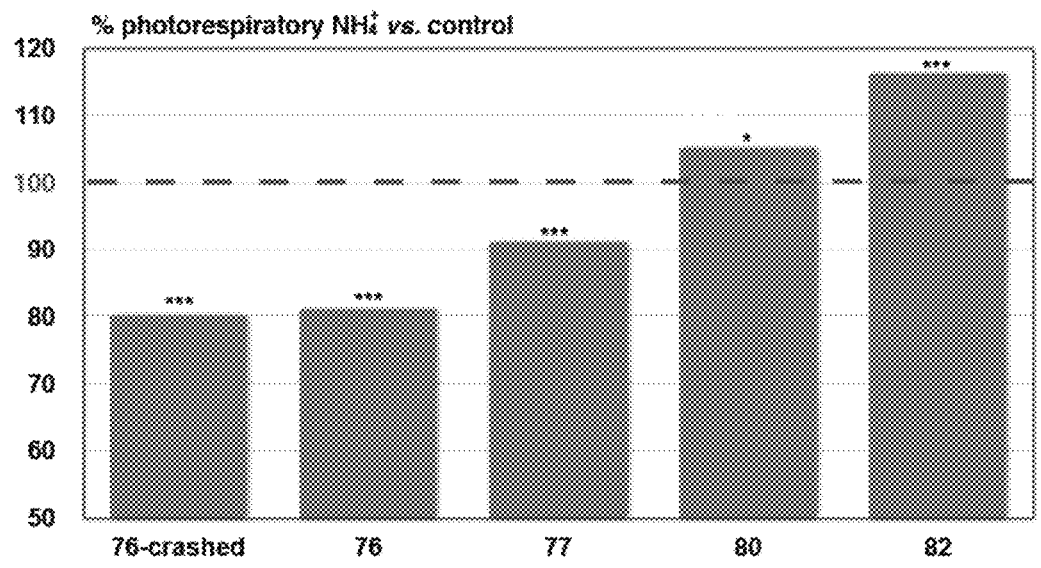
FIG. 7: Photorespiration rate in selected canola populations. The values were % normalized versus the average of the starting line 'Simon'.

In tobacco and cucumber, it was found that decreased complex I capacity result in an increase in photorespiration (Juczczuk et al. Effect of mitochondrial genome rearrangement on respiratory activity, photosynthesis, photorespiration and energy status of MSC16 cucumber (Cucumis sativus) mutant. Physiol. Plant. 131, 527-541 (2007); Priault et al. The lack of mitochondrial complex I in a CMSII mutant of Nicotiana sylvestris increases photorespiration through an increased internal resistance to CO diffusion. J. Exp. Bot. 57, 3195-3207 (2006)). Similarly, we also found that the high respiring Brassica lines have a significant increased photorespiration, while the low respiring lines have a strongly reduced photorespiration (Table 1—FIG. 7). This implies that low respiration (but not a too low respiration as in the LR76-crashed line) correlates with a favorable physiological state, while high respiration correlates with a lower fitness. The specific characteristics of the physiological states indicate that these lines have a higher, respectively lower, stress tolerance (FIG. 4) and field performance (Table 1—FIG. 5). The selected lines and the control line were tested for seed yield in field trials (five locations with three to six replications of ten square meter per line) during three years (Table 1—FIG. 5). Low respiring lines with a high EUE had on average up to 8% higher seed yield versus the control, while high respiring lines with low EUE had on average a seed yield reduction of up to 10%. In fields with moderate drought stress the best high EUE line had 20% higher yield versus the control, while the seed yield of the high respiring and low EUE line dropped 20%. There is a strong positive correlation between EUE and seed yield (Pearson correlation=0.96).

The high efficiency with which the high and low respiring lines were generated starting from an isogenic line and the fact that the selected lines are indistinguishable from each other, based on our AFLP results, suggest that the distinct physiological characteristics of the lines have an epigenetic basis.

Figure 8:
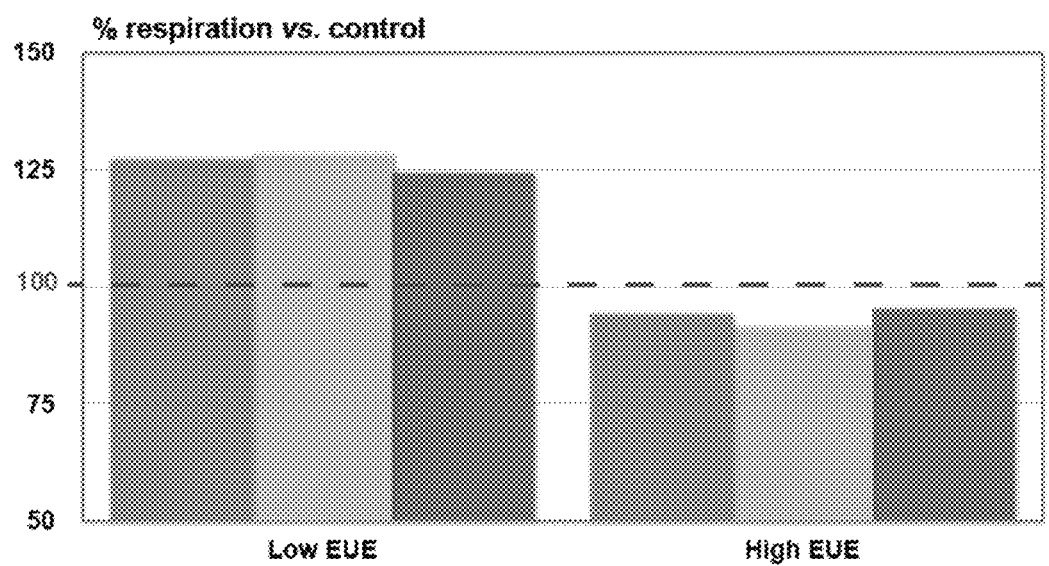
FIG. 8: Cellular respiration rate of progeny plants derived from a cross between selected lines with low, respectively high energy use efficiency and an unselected line. The values were % normalized versus the average of the starting line 'Simon'. Bars on the left of each entry (middle gray) represent values for progeny obtained from selfing lines with high (right half) or low (left half) energy use efficiency. Bars in the middle of each entry (light gray) represent values for progeny obtained from crossing lines with high (right half) or low (left half) energy use efficiency with unselected Simon line, whereby the Simon line is the male plant. Bars on the right of each entry (dark gray) represent values for progeny obtained from crossing lines with high (right half) or low (left half) energy use efficiency with unselected Simon line, whereby the Simon line is the female plant.

From the about eight generations of seed scaling up in the greenhouse and three years of elaborate field trials, it has become obvious that the epigenetic state of the lines is stably inherited by selfings. As described before for the epigenetic recombination component in Arabidopsis (Molinier et al. Transgeneration memory of stress in plants. Nature 442, 1046-1049 (2006)), the epigenetic respiration component of canola can be transmitted in reciprocal backcrosses with a non-selected control line. For example, in the high respiring line HR82, the selfing and the backcrosses to the original Simon line with HR82 as female and male resulted in progenies with respectively 127%, 124% and 128% respiration versus the control. The same was true for the low respiring line LR77 of which the selfing and backcrosses to Simon with LR77 as female and male resulted in progenies with respectively 89%, 91% and 92% versus the control (FIG. 8).

Figure 10:
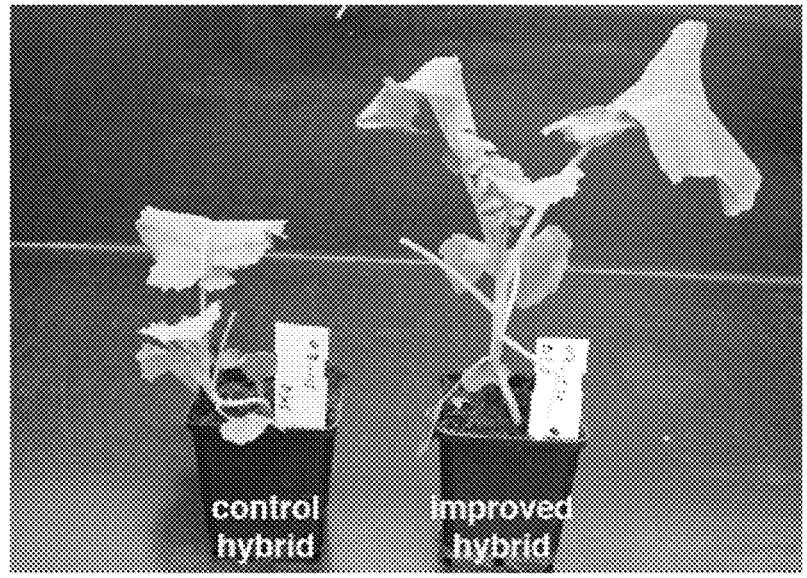
FIG. 10: Comparison between a commercial hybrid plant generated by crossing unselected male and female parents (left) and a hybrid plant generated by crossing male and female parents selected for high energy use efficiency (right).
Figure 11:
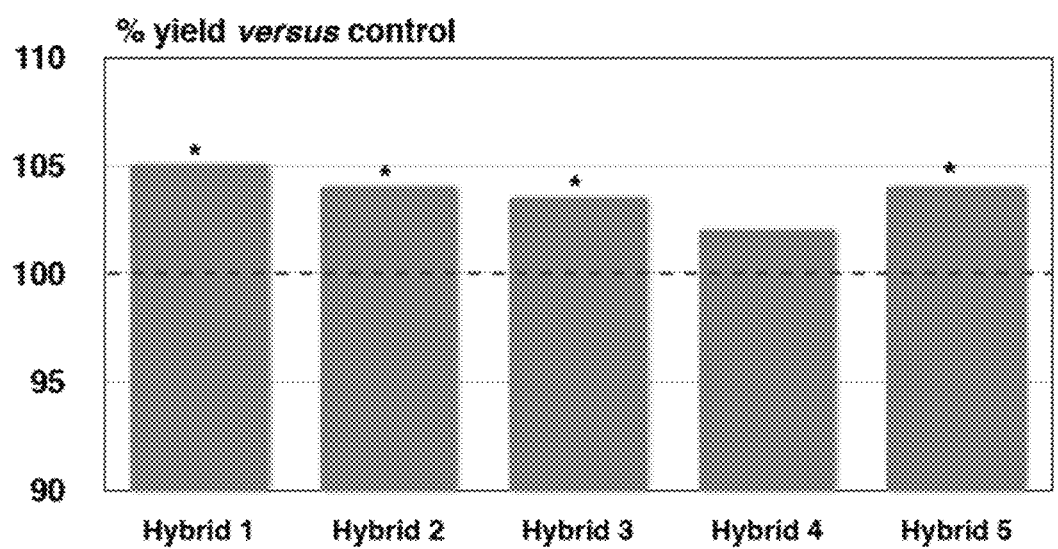
FIG. 11: Seed Yield of hybrid lines generated by crossing male and female parents selected for high energy use efficiency normalized (%) versus a control hybrid plant which was generated by crossing unselected male and female parents.

Our results show that it is feasible to select for a complex trait solely based on directing the epigenetic component. The main difference with the selection in classical breeding schemes is that selection may not only be done at the population but primary at the plant level and this in a recursive way. By applying the same selection schemes on elite parental lines of canola (FIG. 9), we generated hybrids that have up to 5% higher yields additive on the yield increase by heterosis (FIG. 10-11 and Table 2). This shows the general utility of the selection method in canola and confirms the transgenerational stability of the epigenetic respiration component. Experiments further indicate that this type of selection is also feasible in other plant species such as rice and tomato.

TABLE 1

Physiological and agronomical properties of selected canola populations.

| Line | Respiration | NAD(P)H content | EUE | Complex I activity | Ascorbate content | photorespiration | Seed yield Average[1] | Seed yield Field with stress[2] | Seed yield Optimal field[3] |
|---|---|---|---|---|---|---|---|---|---|
| 76-crashed | 74.5*** | 73** | 98 | 140** | 200*** | 80** | 97 | 106 | 97 |
| 76 | 90*** | 98 | 109 | 127** | 208*** | 81** | 104* | 114** | 97 |
| 77 | 92.5*** | 103* | 111 | 120** | 185*** | 91* | 108** | 120** | 103 |
| 80 | 125*** | 99 | 79 | 100 | 79* | 105* | 92** | 81** | 93* |
| 82 | 139*** | 98 | 71 | 95** | 74** | 116** | 90** | 80** | 88** |

Values are normalized versus a control line and expressed in percentage. The control line is the original doubled haploid canola line from which the selected populations are derived, without the recurrent selection.
EUE: Energy use efficiency (=NAD(P)H content divided by respiration)
[1] seed yield as defined on 5 locations; 6 repetitions/location during 3 years
[2] One location with sandy soil and moderate drought stress, 2 years
[3] One location with loamy soil, 3 years
*P < 0.05 versus control
**P < 0.01 versus control
***P < 0.001 versus control

TABLE 2

Physiological and agronomical properties of a hybrid canola line obtained by crossing inbred male and female lines which had been recurrently selected for high energy use efficiency.

| | % versus control hybrid[a] |
|---|---|
| Respiration | 91*** |
| NAD(P)H content | 100 |
| Energy use efficiency | 110 |
| Complex I activity | 125** |
| Ascorbic acid content | 115** |
| Photorespiration | 72** |
| Seed yield[b] | 105* |

[a] Hybrid obtained by crossing the original non-selected female and male
[b] 4 locations, 4 repetitions/location, 1 year
*P < 0.05 versus control
**P < 0.01 versus control
***P < 0.001 versus control

Example 3

Selection and Characterization of Selected *Brassica napus* Plants with High Energy Use Efficiency Combined with Enhanced Drought Tolerance

Figure 12:
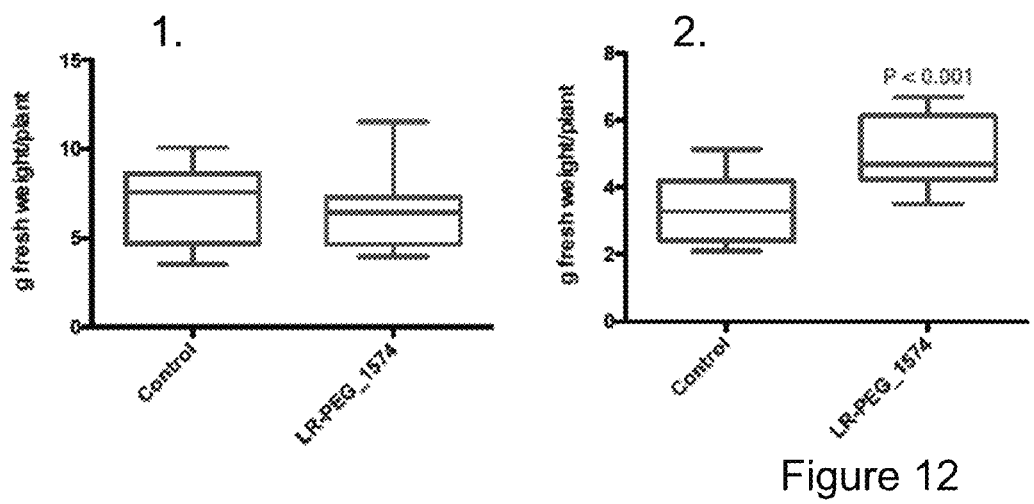
FIG. 12: Growth of sublines selected for high energy use efficiency and drought tolerance. Seeds of selected sublines and control lines were sown. Half of the plants were subjected to normal watering regime. After 8 days, the plants under "drought regime" were no longer provided with water for 8 days, until wilting symptoms become apparent. The soil was moistened. After about 3 days the plants started wilting again. Plants were watered and after 1 day the fresh weight of the plants was determined. Diagram 1 represents the data for control plants and drought tolerant selected lines (LR-PEG__1574) under normal watering. Diagram 1 represents the data for control plants and drought tolerant selected lines (LR-PEG__1574) under a drought regime.
Figure 13:
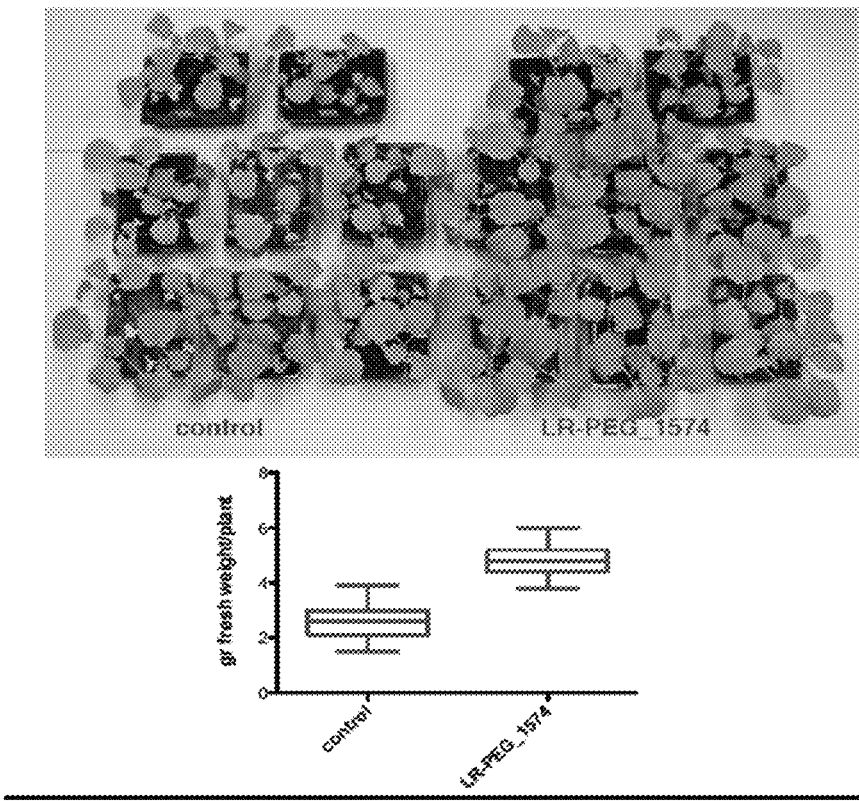
FIG. 13 is a picture of control plants and drought tolerant plants grown under restricted water supply conditions. The diagram below represents the measurements for fresh weight of the control plant and drought tolerant plants.

*Brassica napus* plants were selected as described in Example 2, except that the callus inducing media now contained PEG6000 at a 5% end concentration, mimicking drought conditions. The best line exhibiting high energy use efficiency (LR-PEG__1574) under these growth conditions were grown in comparison with control plants under normal watering conditions and under conditions of restricted water supply. FIGS. 12 and 13 provide a summary of the results of these experiments, demonstrating that LR-PEG__1574 outperforms control plants (isogenetic but not subjected to the high energy use efficiency selection methods) under drought conditions.

The invention claimed is:

1. A method of selecting a population of plants or seeds with a high energy use efficiency comprising the steps of:
   a. providing a population consisting of a plurality of individual plants which are genetically uniform;
   b. isolating a tissue sample or explant from individual plants of said population in a manner which allows further cultivation of said sampled individual plants;
   c. determining the cellular respiration rate of said individual plants by analyzing said sample of said plants;
   d. selecting a number of plants wherein said sample exhibits a cellular respiration which is lower than the average cellular respiration of samples from said population;
   e. growing the selected plants and propagating from each of the selected plants a line of cloned progeny plants;
   f. determining the energy use efficiency for each line of cloned progeny plants;
   g. selecting a line of clone plants wherein said energy use efficiency is higher than the average of the energy use efficiency of all lines of cloned progeny plants;
   h. growing a population of individual plants from said selected line of clone progeny plants; and
   i. repeating at least once steps b to h on said subsequent population.

2. The method according to claim 1, wherein said individual plants are doubled haploid plants.

3. The method according to claim 1 or claim 2, wherein said step is repeated at least twice.

4. The method according to claim 1 or claim 2, wherein said propagating is achieved by self-pollination of said selected plant and harvesting the seeds or by vegetative multiplication.

5. The method according to claim 1 or claim 2, wherein said energy use efficiency is determined by
   a. i. determining the cellular respiration rate in said sample;
      ii. determining the NAD(P)H content in said sample; and
      iii. dividing the NAD(P)H content by the cellular respiration rate to determine the energy use efficiency, or
   b. measuring the ascorbate content in said sample, or
   c. measuring the activity of complex I of the mitochondrial respiratory chain in said sample.

6. The method according to claim 1 or claim 2 wherein the steps of determining the energy use efficiency for each line of cloned progeny plants and selecting a line of clone plants wherein said energy use efficiency is higher comprise:
   a. determining the cellular respiration rate in said samples and at least one of the following parameters:
      i. ascorbate content in said sample;
      ii. NAD(P)H content in said sample;
      iii. activity of complex I of the mitochondrial respiratory chain in said sample; or
      iv. photorespiration in said sample; and
   b. identifying plants with low cellular respiration in said sample and a high ascorbate content, or a high respiratory chain complex I activity or low photorespiration.

7. The method according to claim 6, wherein said cellular respiration rate is between 85 and 95% of the cellular respiration rate of a control plant, and/or wherein said NAD(P)H content is between 95 to 105% of the NAD(P) H content of a control plant, and/or wherein activity of said complex I of the mitochondrial respiratory chain activity is between 120 to 140% of activity of a control plant, and/or wherein said ascorbate content is between 150 to 220% of the ascorbate content of a control plant, and/or wherein said ascorbate content is between 150 to 220% of the ascorbate content of a control plant, and/or wherein said photorespiration is between 80 to 92% of the photorespiration of a control plant.

8. The method according to claim 1 or claim 2, wherein said tissue sample is isolated by severing the hypocotyl from the epicotyl, whereby the hypocotyl constitutes said sample and the epicotyl is further grown to a plant.

9. The method according to claim 1 or claim 2, wherein said plant is a *Brassica* oilseed rape, a tomato plant or a rice plant.

10. A method for producing a population of plants or seeds with increased yield potential, and/or increased vigor and/or increased tolerance to adverse abiotic conditions, comprising selecting a population of plants or seeds with a high energy use efficiency according to claim 1 or claim 2.

11. The method according to claim 10, wherein said plants are further crossed with another plant.

12. A method for increasing harvest yield comprising:
   a. producing a population of plants or seeds with a high energy use efficiency according to claim 1 or claim 2;
   b. growing said plants or seeds in a field;
   c. producing a harvest from said plants or seeds.

13. A method for producing a hybrid plant or hybrid seed with high yield or tolerance to adverse abiotic conditions comprising:
   a. selecting a population of plants with high energy use efficiency according to claim 1 or claim 2 for at least one parent inbred plant;
   b. crossing plants of said population with another inbred plant;

c. isolating hybrid seed of said crosses; and d. optionally, grow hybrid plants from said seed.

14. The method according to claim 13, wherein a population of plants with high energy use efficiency is selected for both parent inbred lines.

15. The method according to claim 13, wherein said one parent inbred plant is a male sterile plant and maintaining said male sterile plant requires the use of a maintainer line having high energy use efficiency.

16. The method of claim 1, wherein between step b) and c) said tissue samples or explants are cultured for 0 to 10 days:

a. under conditions mimicking drought conditions;

b. on a medium containing polyethylene glycol;

c. on a medium comprising sucrose; or d. on a callus inducing medium.

17. The method according to claim 1, wherein at step g) a line of clone plants is selected with the highest energy use efficiency of all lines of cloned progeny plants.

* * * * *